US011752072B2

(12) United States Patent
Carlson et al.

(10) Patent No.: US 11,752,072 B2
(45) Date of Patent: Sep. 12, 2023

(54) QUICK SET CEMENTS FOR DENTAL PULP CAPPING AND RELATED METHODS OF USE

(71) Applicant: University of Utah Research Foundation, Salt Lake City, UT (US)

(72) Inventors: Krista L. Carlson, Salt Lake City, UT (US); John S. Colombo, Salt Lake City, UT (US); Steven E. Naleway, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 299 days.

(21) Appl. No.: 16/816,197

(22) Filed: Mar. 11, 2020

(65) Prior Publication Data

US 2020/0289378 A1  Sep. 17, 2020

Related U.S. Application Data

(60) Provisional application No. 62/816,613, filed on Mar. 11, 2019.

(51) Int. Cl.
*A61K 6/54* (2020.01)
*A61K 6/836* (2020.01)
(Continued)

(52) U.S. Cl.
CPC ............... *A61K 6/54* (2020.01); *A61K 6/833* (2020.01); *A61K 6/836* (2020.01); *A61K 6/84* (2020.01); *A61K 6/69* (2020.01)

(58) Field of Classification Search
CPC ...................................................... A61K 6/54
See application file for complete search history.

(56) References Cited

U.S. PATENT DOCUMENTS 1,621,793 A  3/1927 Kruger
2,516,438 A  7/1950 Wheeler
(Continued)

FOREIGN PATENT DOCUMENTS

CA        3059479 A1 * 10/2018 ............... A61K 6/16
WO   WO-2010098305 A1 *  9/2010 ............... A61F 2/28
(Continued)

OTHER PUBLICATIONS

English machine translation of Nakamura et al. (WO 2010/098305) (Year: 2010).*
(Continued)

*Primary Examiner* — Michael F Pepitone
(74) *Attorney, Agent, or Firm* — Thorpe North & Western, LLP; Erik S. Ericksen

(57) ABSTRACT

A dental pulp capping composition can comprise a particulate base material which is non-toxic, and capable of forming a structural capping matrix; and a particulate setting material which is non-toxic, water-soluble, biocompatible, and capable of setting the composition. Optional growth factors can also be introduced into the composition to facilitate dental tissue repair. A complimentary method of restoring damaged tooth features can comprise removing diseased and/or damaged portions of the tooth to expose a prepared tooth region. Water can be added to the dental pulp capping composition to form a workable coherent paste. The workable coherent paste can be introduced into the prepared tooth region. The workable coherent paste can then be shaped within the prepared tooth region and then set to form a rigid biomimetic structure within the prepared tooth region.

26 Claims, 10 Drawing Sheets

(51) Int. Cl.
*A61K 6/84* (2020.01)
*A61K 6/833* (2020.01)
*A61K 6/69* (2020.01)

(56) References Cited

U.S. PATENT DOCUMENTS

| | | | |
|---|---|---|---|
| 2,877,199 A | | 3/1959 | Taub |
| 3,255,079 A | | 6/1966 | Schroeder et al. |
| 3,367,788 A | | 2/1968 | Sheldon et al. |
| 3,390,456 A | | 7/1968 | Deleva |
| 3,913,229 A | | 10/1975 | Driskell et al. |
| 4,097,935 A | | 7/1978 | Jarcho |
| 4,518,430 A | | 3/1985 | Brown et al. |
| 4,813,876 A | | 3/1989 | Wang |
| 5,252,121 A | | 10/1993 | Arnold |
| 5,296,026 A | | 3/1994 | Monroe et al. |
| 5,342,441 A | | 8/1994 | Mandai et al. |
| 5,415,547 A | | 5/1995 | Torabinejad et al. |
| 5,522,893 A | | 6/1996 | Chow et al. |
| 5,525,148 A | | 6/1996 | Chow et al. |
| 5,735,942 A | | 4/1998 | Litkowski et al. |
| 5,891,233 A | | 4/1999 | Salonen et al. |
| 6,002,065 A | * | 12/1999 | Constantz ............... A61L 27/12 423/317 |
| 6,054,400 A | | 4/2000 | Brink et al. |
| 6,379,453 B1 | | 4/2002 | Lin et al. |
| 6,398,859 B1 | | 6/2002 | Dickens et al. |
| 6,479,565 B1 | | 11/2002 | Stanely |
| 7,942,961 B2 | | 5/2011 | Asgary |
| 8,722,100 B2 | | 5/2014 | Lovschall et al. |
| 8,979,991 B1 | | 3/2015 | Torabinejad et al. |
| 9,186,433 B2 | | 11/2015 | Yoshida et al. |
| 2003/0159618 A1 | * | 8/2003 | Primus ..................... A61K 6/77 106/737 |
| 2003/0167967 A1 | | 9/2003 | Narhi et al. |
| 2008/0085948 A1 | * | 4/2008 | Primus ..................... A61K 6/78 523/116 |
| 2011/0281241 A1 | | 11/2011 | Pandolfelli et al. |
| 2013/0023601 A1 | * | 1/2013 | Ogliari ..................... A61K 6/851 523/116 |
| 2014/0248322 A1 | * | 9/2014 | Karlinsey ............... A61K 6/816 424/57 |
| 2016/0038380 A1 | * | 2/2016 | Primus ..................... A61K 6/853 424/501 |
| 2018/0116915 A1 | | 5/2018 | Alshwaimi et al. |
| 2019/0060523 A1 | * | 2/2019 | Bakry ....................... C03C 3/19 |
| 2020/0009021 A1 | * | 1/2020 | Oh ........................... A61K 6/849 |

FOREIGN PATENT DOCUMENTS

| | | | | |
|---|---|---|---|---|
| WO | WO 2013/057519 A1 | | 4/2013 | |
| WO | WO-2018014120 A1 | * | 1/2018 | ............ A61K 6/864 |
| WO | WO-2018164436 A1 | * | 9/2018 | ........... A61K 6/0038 |

OTHER PUBLICATIONS

Asgary et al.; "A comparative study of histologic response to different pulp capping materials and a novel endodontic cement." OOOOE; Elsevier; Oct. 2008; vol. 106, Issue 4; pp. 609-614.

Hilton.; "Keys to Clinical Success with Pulp Capping: A Review of the Literature." Operative Dentistry; 2009; vol. 34, Issue 5; pp. 615-625.

Nowicka et al.; "Response of Human Dental Pulp Capped with Biodentine and Mineral Trioxide Aggregate." Journal of Endodontics; Elsevier; Jun. 2013; vol. 39, Issue 6; pp. 743-747.

Sahai.; "Silicate Biomaterials for Orthopaedic and Dental Implants." Reviews in Mineralogy and Geochemistry; Mineralogical Society of America; 2006; vol. 64; pp. 1-31.

Qureshi et al.; "Recent Advances in Pulp Capping Materials: An Overview." Journal of Clinical and Diagnostic Research; Jan. 2014; vol. 8, Issue 1; pp. 316-321.

* cited by examiner

QUICK SET CEMENTS FOR DENTAL PULP CAPPING AND RELATED METHODS OF USE

RELATED APPLICATION

This application claims priority to U.S. Provisional Application No. 62/816,613, filed Mar. 11, 2019 which is incorporated herein by reference.

GOVERNMENT INTEREST

None.

BACKGROUND

Vital pulp therapies aim to create healthy microenvironments that promote the natural healing of dental pulp and a timely formation of a new dentinal bridge between restorations and voids created due to carious incursion or trauma as generally illustrated in FIG. 1. Dental caries are the most common human communicable disease, affecting 92% of the population between 16 and 65 in the U.S., with as many as 50% of dental restorations failing within 10 years. Retreatment of a restoration involves the repeated removal of mineralized tissues, increasingly compromising the structural integrity of the tooth and significantly raising the chances of pulpal involvement. Each year, over 24 million individuals endure root canal therapy to remove diseased pulp tissue and this often leads to expensive restorations to preserve residual dentin that becomes brittle and prone to fractures. Both direct and indirect pulp capping in adults have variable success, with deep carious lesions or partial pulp exposures often requiring full endodontic treatment or extraction in cases where patients cannot afford these costly procedures. The challenges inherent in developing materials which enhance the success rates of pulp capping by allowing the rapid formation of a dentin bridge in apposition to a new restoration are significant; however, the potential benefits to patients are highly promising and could change the way care is delivered when treating deep carious or pulp exposures.

Very often, with a low remaining dentin thickness, the vitality of the pulp is threatened, necessitating root canal therapy or extraction, depending on a multitude of factors, including the financial status of the patient. In these cases, pulp-capping techniques may be employed in an attempt to avoid an extraction or costly root canal therapy. Despite the advances in pulp capping materials, the most common pulp capping materials currently in use are DYCAL (calcium hydroxide) and mineral trioxide aggregate (MTA), many are still somewhat toxic to the complex pulp tissues or are not particularly effective at stimulating a rapid formation of the dentin bridge. As a result, pulp capping still has mixed results in practice. Central to the processes of dentin bridge formation and the success of pulp capping are the vitality of odontoblasts and dental pulp cells that have the capacity to form both new dentin matrix and pulp tissue. Additionally, the pool of mesenchymal progenitor cells in dental pulp or dental pulp progenitor cells, DPPCs, underscores the pulp's innate capacity for self-repair through the production of reactionary and reparative dentin. Current materials in use for pulp capping do not capitalize fully on this capacity for repair, as they are not reflective of naturally occurring materials found in dentin.

When considering any new pulp capping material, comparison to the 'gold standard' DYCAL, a calcium hydroxide (CaOH) paste that can be easily manipulated and sets under 10 min is advisable. Dissolution during setting leads to high pH which acts as an antibacterial/bacteriostatic and hemostatic agent, as well as stimulating odontoblasts to form reparative dentin. Issues with this material include problems with adhesive and sealing abilities, poor mechanical properties, and dissolution over time. To improve upon the issues with sealing and physical integrity after placement, MTA was created which combined compounds similar to Portland cement. In phosphate containing body fluids, the MTA matures into a calcium deficient hydroxyapatite. However, MTA has problems during user manipulation and placement, and has a long setting time of 2-4 hrs depending on conditions.

Ultimately, dental pulp is a unique microenvironment that gives the tooth vitality and the adaptability to survive repeated cyclical loading. This tissue is particularly sensitive to insult through trauma or microbial incursion, both of which lead to pulpal inflammation, tissue destruction and pulpal necrosis. Irreversible damage to the dental pulp can lead to the necessity of costly root canal therapy and can ultimately result in a devitalized tooth more prone to fracture. Therefore, there is significant interest in vital pulp therapy, the ultimate goal of which is the creation of a healthy microenvironment that promotes the natural healing of dental pulp, supporting revascularization, soft tissue regeneration and the timely formation of a dentin bridge between restorations and the mineralized tissues of the tooth. Currently, pulp capping, both direct and indirect, when employed in adults in an attempt to preserve the vitality of damaged dental pulp, has relatively poor success rates.

SUMMARY

A chemically bonded ceramic (CBC) pulp capping material that combines quick setting behavior with sealing ability, strength, and chemical durability, can lead to more consistent and predictable clinical outcomes. Additionally, the use of material with a uniform and/or predictable particle size can enable controlled functionalization and release kinetics of growth factors.

A dental pulp capping composition can comprise a particulate base material which is non-toxic, and capable of forming a structural capping matrix; and a particulate setting material which is non-toxic, water-soluble, biocompatible, and capable of setting the composition.

A complimentary method of restoring damaged tooth features can comprise removing diseased and/or damaged portions of the tooth to expose a prepared tooth region. Water can be added to the dental pulp capping composition to form a workable coherent paste. The workable coherent paste can be introduced into the prepared tooth region. The workable coherent paste can then be shaped within the prepared tooth region. The shaped workable coherent paste can then be set to form a rigid biomimetic structure within the prepared tooth region. In some cases, the shaped workable coherent paste can also maintain a shape once formed (i.e. not flowable under operating conditions).

A dental pulp capping kit can comprise the dental capping composition as a dry composition. Such a kit can also include instructions to add water to the dry composition to form a workable coherent paste consistent with the descriptions herein.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

Figure 1:
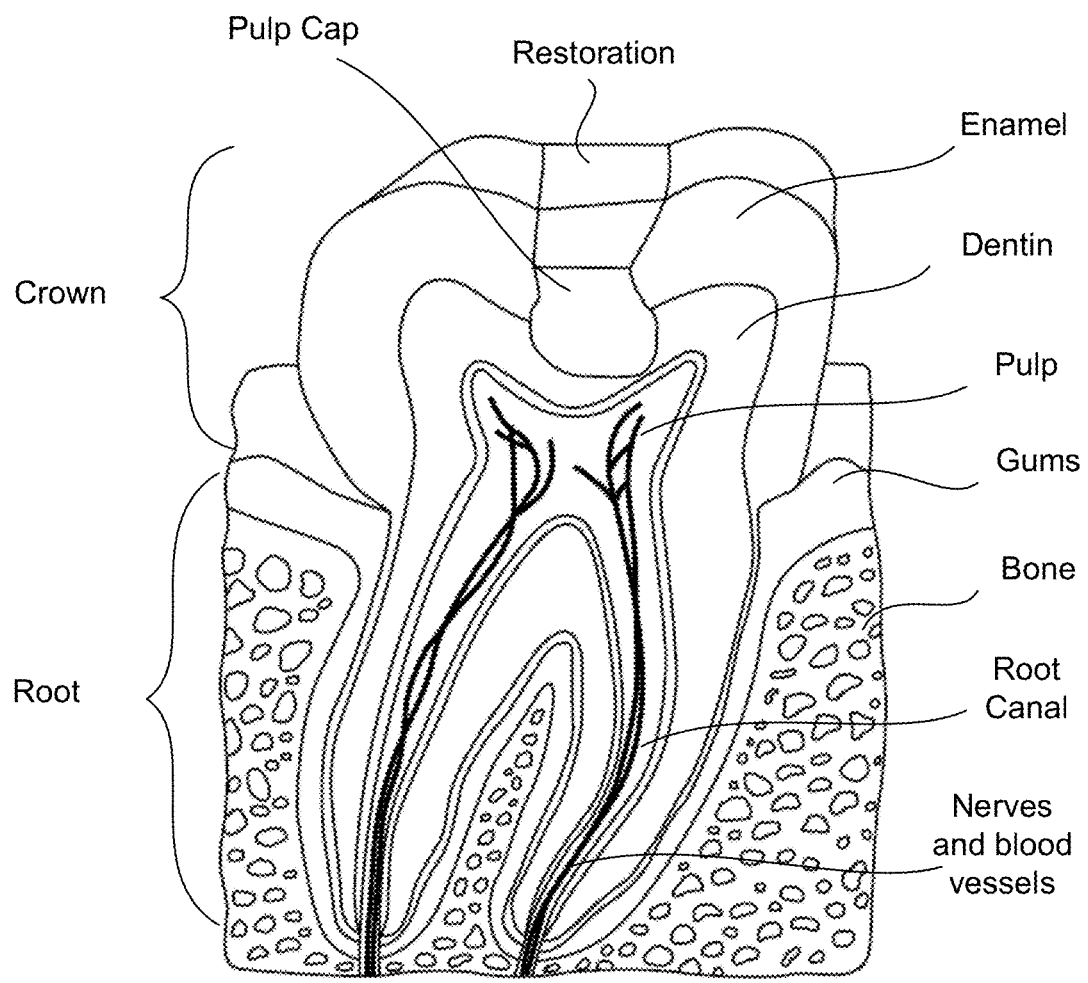
FIG. 1 is a schematic of a dental restoration.

These drawings are provided to illustrate various aspects of the invention and are not intended to be limiting of the scope in terms of dimensions, materials, configurations, arrangements or proportions unless otherwise limited by the claims.

DETAILED DESCRIPTION

While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

Definitions

In describing and claiming the present invention, the following terminology will be used.

The singular forms "a," "an," and "the" include plural referents unless the context clearly dictates otherwise. Thus, for example, reference to "a particle" includes reference to one or more of such materials and reference to "introducing" refers to one or more such steps.

As used herein, the term "about" is used to provide flexibility and imprecision associated with a given term, metric or value. The degree of flexibility for a particular variable can be readily determined by one skilled in the art. However, unless otherwise enunciated, the term "about" generally connotes flexibility of less than 1%, and in some cases less than 0.01%.

As used herein, "biocompatible" refers to a material which does not elicit a negative response from contacted tissue. "Bioactive" material elicits biologically favorable conditions between the material and adjacent tissue in the context of tissue repair and regeneration. In some cases, the particulate base material is a bioactive material with respect to at least one of dental pulp, dentin, cementum, tissues of the periodontium, oral mucosa and their associated vasculature.

As used herein, "frit" refers to a particulate ceramic material which is irregular in shape. Frit can be used as provided or spheroidized.

As used herein, "glass" refers to a ceramic with no long-range atomic order and experiencing a glass transition upon heating, while "ceramic" can refer to any inorganic compound of a non-metal or metalloid which can be crystalline, semi-crystalline, vitrified, or amorphous.

As used herein, "non-toxic" refers to a property of a material that does not adversely effects tissue health as compared to the same tissue left unexposed to such material. Of particular concern in this context is non-toxic materials with respect to dental pulp and dentin under body temperatures of about 96-105° F. A non-toxic material does not cause cell death, either by directly causing the destruction of cells and tissues or through the induction of programmed cell death (apoptosis).

As used herein, "water-soluble" means that at least a portion of the material dissolves in the presence of water at normal body temperatures (e.g. within about 5° F. of 98.6° F.).

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, the term "at least one of" is intended to be synonymous with "one or more of" For example, "at least one of A, B and C" explicitly includes only A, only B, only C, and combinations of each.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Dental Pulp Capping Compositions

Pulp capping material can be non-toxic to pulp, adherent to the mineralized tissues of the tooth, display good mechanical and chemical durability over time, and be effective at stimulating dentin production by resident dental pulp cells, incorporating itself into a rapidly formed dentin bridge in apposition to an overlying restorative material.

In order to develop dental pulp capping materials with enhanced properties, the corrosion behavior of the materials and final hardened products in a biological milieu can be considered. Further, the material's corrosion and hardening influence on the pulp cells and pulpal tissues can be addressed. A novel quick setting dental pulp cap composition can be produced by mixing a particulate base material to form a structural capping matrix with a particulate setting material to produce a CBC. This CBC is comprised of a quick set material and a chemically stable material and can provide predictable control over the set time and final material properties, as well as the optional introduction and release of desirable growth factors into the system.

A dental pulp capping composition can comprise a particulate base material which is non-toxic, and capable of forming a structural capping matrix; and a particulate setting material which is non-toxic, water-soluble, biocompatible, and capable of setting the composition.

The morphology of the particulate materials can effect performance of the composition during use. In one example, one or both of the particulate base material and the particulate setting material are microspheres. Such microspheres can provide a more uniform a predictable dissolution, growth factor release profile, and other benefits as described herein. Alternatively, one or both of the particulate base material and the particulate setting material can be frit. In another case, at least a portion of the particulate materials can be microspheres, and in some cases at least 50%.

Particle size can also help to improve workability and shaping of the composition during use within cavities or regions of the tooth. As a general guideline, one or both of the particulate base material and the particulate setting material have an average maximum particle dimension of 0.1 µm to 100 µm, and in some cases up to 500 µm, and in some cases from about 0.1 µm to about 10 µm. As a general guideline, uniform spherical particles can improve performance. Such particles can be formed by spheroidization or other suitable techniques. Collections of spherical particles can include some non-spherical particles but are generally greater than about 80% spherical. In one alternative, one or both of the particulate base material and the particulate setting material can have a bimodal or multi-modal distribution of sizes including a first particle size which is at least 20% larger than a second particle size. Such distribution of sizes can decrease setting time since smaller particles degrade faster than relatively larger particles of the same composition. Optionally, these particulate materials can be annealed by heating sufficient to reduce or remove residual stresses. Such annealing can also increase rate of degradation compared to as-formed microspheres.

As a general guideline, the particulate base material can be any material that is non-toxic to surrounding dental tissue, forms a structural matrix which physically protects underlying dental pulp or other native tissue, produces a desired hardness, and chemical durability. Although properties can vary, approximating mechanical properties of dentin can be desirable. Accordingly, a Vicker's hardness of 40-70 VHN, and a strength Young's modulus of 15 to 30 GPa can be particularly suitable for the set material. As described herein, in some cases it can also be desirable for the base material to decompose to form hydroxyapatite (i.e. act as a hydroxyapatite precursor). Such materials can stimulate endogenous dentin bridge formation. Many bioactive silicate, phosphate and borate ceramics can exhibit such decomposition behavior. As an example, the particulate base material can be generally selected from the group consisting of ceramics, glasses, crystalline materials, and combinations thereof, including ceramic-metal composites, ceramic-polymer composites, and the like. In one more specific example, the particulate base material can be at least one of aluminate glass, silicate glass, phosphate glass, and composites thereof. Alternatively, the particulate base material is at least one of aluminate, silicate, phosphate, and composites thereof as crystalline or semi-crystalline materials. In another specific example, the particulate base material can be at least one of calcium aluminate glass (CaAl; 60CaO 40Al$_2$O$_3$ mol %), mineral trioxide aggregate, calcium metaphosphate glass (40CaO-60P$_2$O$_5$), SiO$_2$—CaO—Na$_2$O—P$_2$O$_5$ silica glass (e.g. BIOGLASS 45S5, 45S5.4F, 52S4.6, KGC CERAVITAL, and the like), SiO$_2$—CaO—P$_2$O$_5$ silica glass, calcium silicate glass, calcium phosphate silica glass, hydroxyapatite, calcium phosphate glass (CaP), calcium hydroxide (e.g. DYCAL), and composites thereof. MTA is generally a refined Portland cement mixed with bismuth oxide, e.g. dicalcium silicate, tricalcium aluminate, tricalcium silicate, bismuth oxide, and optional tetracalcium aluminoferrite (which is commercially available as white or gray PROROOT from Dentsply International Inc.). The bismuth oxide acts as a radiopacity enhancing agent, although other radiopacity agents can be used.

In some cases, hydroxyapatite particulate can be added directly as the particulate base material, rather than relying on chemical conversion of a ceramic into hydroxyapatite. Although hydroxyapatite can be used alone as the base material, in some cases it can be advantageous to include a second hydroxyapatite precursor ceramic material as described herein. For example, a hydroxyapatite to hydroxyapatite precursor weight ratio may be 0.1:1 to 2:1, and in most cases 0.8:1 to 1:4.

Alternatively, metal base material can be used. As one example, the metal particulate base material can comprise titanium. In one example, commercially pure titanium, titanium oxides, or Ti-6Al-4V can be used. In order to improve osteointegration hydroxyapatite or hydroxyapatite precursor coatings can be added to such metal materials. Such coatings can be formed by chemical vapor deposition, plasma spray coating, electrodeposition, physical vapor deposition, and the like.

As a general guideline, the particulate base material comprises 1% to 90% by weight of the composition, and in some cases 50% to 90% by weight of the composition. In another example, the particulate base material can comprise 50 to 80% by weight of the composition, and in one example can be about 75% by weight.

The particulate setting material can be a material which is non-toxic (especially to dental tissue), biocompatible, and capable of setting the composition. Working and setting times can be quantified by using a Gillmore needle apparatus under standard ISO 9917-2:2017. Generally, working time is associated with a time that the material is no longer malleable, while setting time refers to a time when the material reaches a final maximum hardness. As a general guideline, the particulate setting material can be selected from the group consisting of metasilicate glass, bioactive borate glass, and the like. More specific examples of particulate setting material can include sodium silicate blend, potassium silicate, calcium silicate, borate glasses, and combinations thereof. Non-limiting examples of particulate setting material can include $Na_2O$—$SiO_2$, $Na_2O$—$CaO$—$SiO_2$—$P_2O_5$, $Na_2O$—$CaO$—$B_2O_5$, $K_2O$—$CaO$—$B_2O_3$, sodium metasilicate (NaSi) glass, and combinations thereof. In one specific example, the particulate setting material is NaSi ($50Na_2O$ $50SiO_2$ mol %).

Often, the particulate setting material dissolves upon exposure to water and forms a gel. In some cases the particulate setting material can produce heat upon dissolution in water. Such exothermic dissolution can provide desirable heat energy to increase setting reaction rates and decrease setting times. Such heat can also contribute to initial formation of hydroxyapatite, depending on the particulate base material. Full formation of hydroxyapatite or other setting crystals can occur over a period of days or weeks.

In some cases an alkali or alkaline earth metal salt can be used as a setting agent or to promote setting of the particulate setting material. Non-limiting examples can include calcium chloride, magnesium sulfate, aluminum sulfate, zinc oxide, sodium silicofluoride, sodium borate, and the like.

Although proportions can vary, as a general guideline, the particulate setting material comprises 10% to 99% by weight of the composition, and in some cases 20% to 50% by weight of the composition.

The resulting dental pulp capping composition can have a desirable balance of working time and setting time (upon mixing with water). In one example, the composition has a working time of at least one minute, and a setting time of less than 30 minutes. In some cases, the working time can be 4 to 10 minutes, while the setting time can be less than 20 minutes (i.e. and greater than the working time). Although setting times can often be less than 30 minutes, hydroxyapatite can continue to crystallize and form over a longer period ranging from several days to several weeks. Working times will always be less than setting times.

Additional components can be optionally added to refine the dental pulp capping composition for particular environments, tailoring of properties, and the like. Non-limiting examples of potential additives include inert fillers, pH control agents, setting time adjustment agents, colorants, antimicrobials, radiopacity agents, working time adjustment agents, corrosion accelerants, corrosion inhibitors, and combinations thereof. Non-limiting examples of inert filler include at least one of silica, quartz, and carbon black. Non-limiting examples of suitable pH control agent is calcium hydroxide. Non-limiting examples of suitable setting time adjustment agent is at least one of gypsum, Non-limiting examples of suitable colorants are at least one of titanium dioxide, dyes, carbon black, and composites thereof. Colorants can aid practitioners in visually confirming locations of the paste compared to adjacent materials or tissue but are not typically needed for aesthetics since these compositions will normally be ultimately embedded underneath other dental restoration materials or implants. Non-limiting examples of suitable antimicrobial can include silver. Radiopacity agent can generally comprise bismuth, although non-limiting examples of radiopacity agents include bismuth oxide, zinc oxide, lead oxide, bismuth subnitrate, bismuth carbonate, barium sulfate, iodoform, calcium tungstate, and zirconium oxide.

In order to facilitate and encourage formation of a dentin bridge, pulp recovery, or other dental tissue repair, the dental pulp capping compositions can optionally be used as a vehicle for delivery of particular growth factors to the affected area. Non-limiting examples of suitable growth factor can include BMP-2, VEGF, G-CSF, TGFβ1, FGF-2, PDGF, and combinations thereof. The growth factor can be distributed within the composition or associated with at least one of the particulate base material and the particulate setting material via electrostatic attraction. Alternatively, the growth factor can be functionalized to one or both of the base and setting materials. In another alternative, the growth factor can be encapsulated in an inorganic shell which degrades upon exposure to water or setting conditions. Non-limiting examples of inorganic shell materials can include, calcium phosphates, sodium silicates, and the like.

Uniform microspheres can aid in accurately predicting surface area which, in turn, allows accurate and predictable functionalization of the microspheres. Microspheres functionalized with BMP-2, VEGF, and G-CSF or other growth factors can stimulate signals of pulpal repair in an ex vivo model of intact pulp tissue more than application of MTA or DYCAL. The composition can also provide separation of the chemically stable and quick set materials with two different biocompatible microsphere components to achieve the combination of the best properties from the DYCAL and MTA.

Notably, when the particulate material are microspheres, corrosion rate and surface area can be more precisely controlled and estimated. This can also aid in controlled release of growth factors and alignment of growth factor loadings with desired delivery concentrations and release kinetics. However, as a general guideline, growth factor loading in the composition can range from about 1 μg growth factor per ml of material and up to 5 μg growth factor per ml of material, although other loading above this range may be suitable.

Notably, these compositions can provide a microsphere based-pulp capping CBC with adjustable surface charge properties allowing relatively simple electrostatic attachment and release of bioactive factors. The physical properties of this dental pulp composition material can be altered to allow simple handling and application to defects or cavity preparations, having a consistency and workability similar to DYCAL. These materials can also have tunable surface charges which can be used to incorporate a variety of bioactive factors and their release manipulated by screening surface charges or local alterations in pH, giving a highly degree of applicability with the potential to be useful in a variety of biomedical applications.

Figure 2:
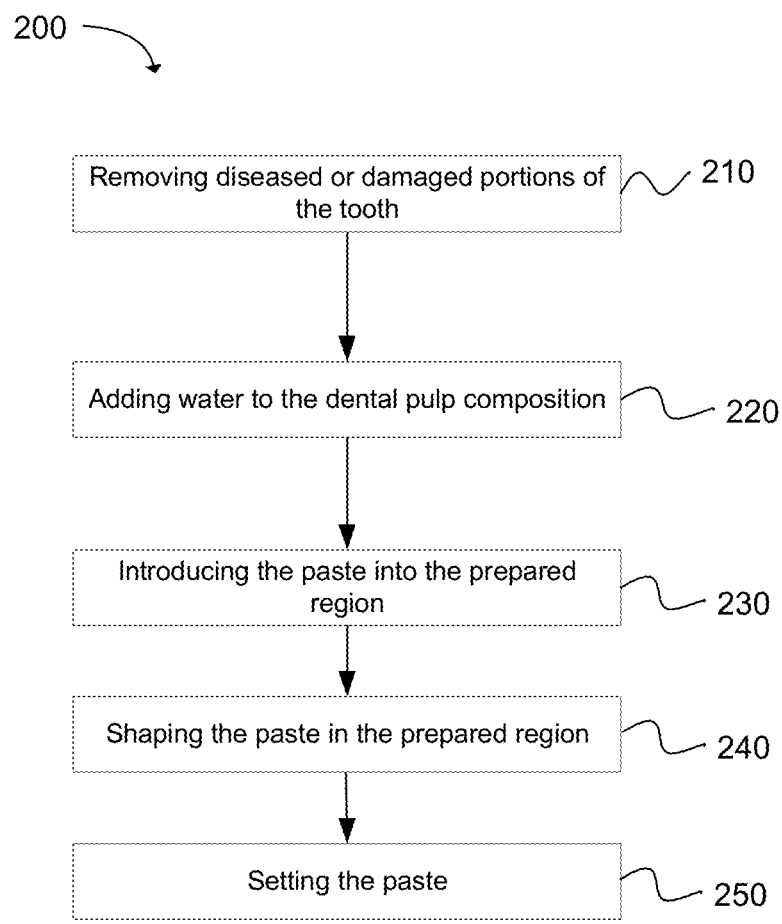
FIG. 2 is a flow diagram of a method of restoring damaged tooth features in accordance with one aspect.

As generally illustrated in FIG. 2, a complimentary method 200 of restoring damaged tooth features can comprise removing diseased and/or damaged portions of the tooth to expose a prepared tooth region 510.

Water can be added to the dental pulp capping composition to form a workable coherent paste 220. In some cases, the water can be deionized and/or sterile water comprising from 10% to 40% by weight of the workable coherent paste.

The workable coherent paste can be introduced into the prepared tooth region 230.

The workable coherent paste can then be shaped within the prepared tooth region 240. Typical working temperatures can range from 23° C. to about 70° C.

The shaped workable coherent paste can then be set to form a rigid biomimetic structure within the prepared tooth region 250. In some cases, the shaped workable coherent paste can also maintain a shape once formed (i.e. not flowable under operating conditions).

The dental pulp capping composition can be particularly suitable for capping of dental pulp but can also be advantageous for other similar applications such as, but not limited to, root canals, root perforation, apical plugs during apexification, pulpotomy, root canal therapy root perforation repair, root end filling, addressing internal root resorption, regenerative endodontics, and the like. Accordingly, in one case, the prepared tooth region includes a dental pulp and adjacent dentin such that the method is capping a dental pulp. In another case, the method is sealing a tooth root canal during an apicoectomy. In yet another case, the method is sealing a root perforation.

A dental pulp capping kit can comprise the dental capping composition as a dry composition. Such a kit can also include instructions to add water to the dry composition to form a workable coherent paste consistent with the descriptions herein.

In situ, CBC can be a primary inorganic component of biologically occurring mineralized tissues in which a number of naturally occurring growth factors are sequestered within the protein extracellular matrix. Damage to these tissues results in the release of numerous sequestered bioactive factors that in turn stimulate a repair process. In dentistry this is routinely exploited clinically as the biological basis for etching a cavity preparation prior to the placement of a restoration, removing the smear layer and stimulating the release of odontogenic growth factors from surrounding dentin. Similarly, etching bone slabs with a variety of agents has been shown to directly release bioactive factors, particularly TGFβ1, which enhance odontoblast like cell differentiation. The dental pulp capping compositions can have a controlled, regular size that can be formed into scaffolds that have negative and positive surface charge characteristics at physiological pH, allowing the electrostatic attachment of a variety of functional proteins. By utilizing this CBC as a pulp capping material which can deliver pro-regenerative growth factors through the controlled manipulation of surface charge, the receptivity and reaction of resident odontoblasts, pulp cells and DPPCs to such materials can be greatly enhanced.

Example 1

Figure 3A:
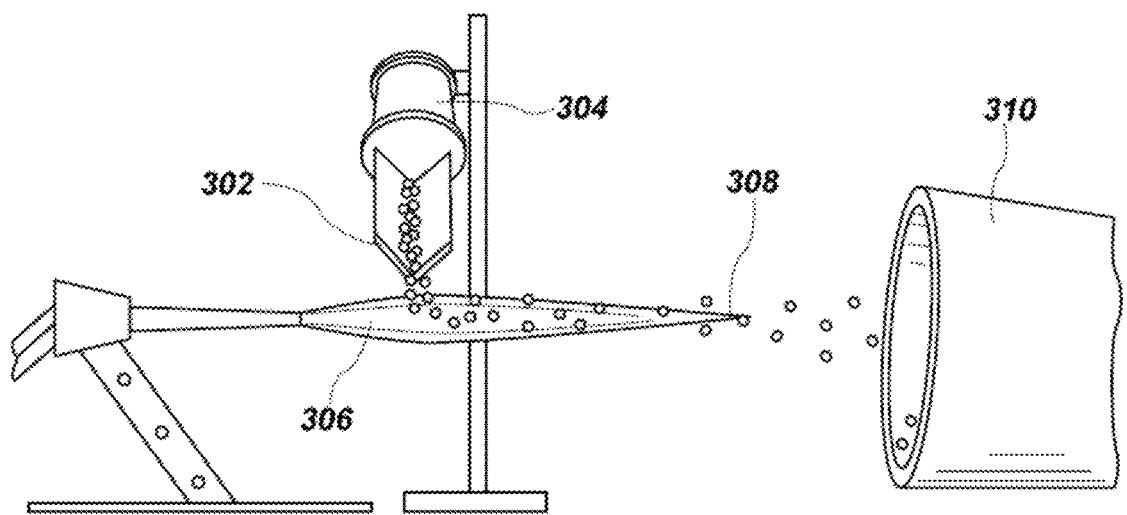
FIG. 3A is a schematic diagram of the spheroidization process to form a mixture of biocompatible microspheres comprised of calcium aluminate and sodium metasilicate to form a chemically bonded ceramic (CBC).
Figure 3B:
FIG. 3B is an SEM of a frit prior to spheroidization in accordance with Example 1.
Figure 3C:
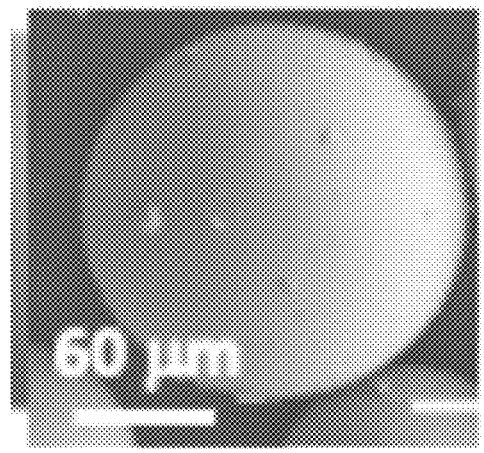
FIG. 3C is an SEM of a spheroidized particle in accordance with Example 1.

A spheroidization process, diagrammed in FIG. 3A, was performed to make microspheres of the CaAl and NaSi. Melt-derived glasses were formed, crushed into a frit, as shown in FIG. 3B and then sieved to the desired particle range. During spheroidization, the fit 302 is dropped from a vibrating spatula 304 into a flame 306 above the melting temperature of the glasses so as to liquefy the frit. In this example, an oxygen-propane flame at 2500° C. The components of the molten liquid will exert attractive forces on one another, creating surface tension. Since the liquid is surrounded by the flame or air, the liquid components experience a net attractive force that points towards the interior of the liquid. This attractive force causes the contraction of the liquid surface until the repulsive force begins to inhibit this behavior. Since the surrounding gases have negligible impact on the liquid, the droplets will form into a spherical shape as microspheres 308 to minimize the surface area for a given volume. The microspheres 308 can be collected using a suitable collector 310 (e.g. container, aluminum foil, or the like). FIG. 3C is an SEM of a microsphere subsequent to collection. Using this process, microspheres between 40-400 μm were fabricated. Although spheroidized simultaneously, the base material and setting material can be spheroidized separately and then mixed.

The corrosion behavior of the CaAl micro spheres was originally examined to try to intrinsically alter the surface charge of microspheres at physiological pH for enhanced adsorption of nucleic acids from cell lysate (i.e., choose a glass chemistry that would provide a positive surface charge instead of the negative surface charge that silicate glasses typically display). It was found that calcium aluminate-based microspheres provided superior adsorption over silicate glasses because of minimization in surface charge repulsion. Release of the nucleic acid was achieved by rinsing the surface with a standard elution buffer.

While some of the calcium aluminate compositions with iron or silica were chemically stable during this process, the pure CaAl microspheres were not, exhibiting corrosion which made them unsuitable candidates for this application. It was observed that the corrosion behavior between the glass and its crystalline counterparts typically utilized in calcium aluminate-based cements were different with the glass exhibiting more pronounced surface swelling and faster setting. Additionally, it was observed that microspheres of the CaAl glass would set faster than frit of the same composition due to the extra dehydration experienced by the glass as it passed through the flame during the spheroidization process. Although agglomeration and setting occurred with the CaAl microspheres, longer time periods are needed for setting and eventual maturation into the chemically durable phases.

Sodium metasilicate is a highly water-soluble glass and readily dissolves in the aqueous solution concurrently with the release of calcium ions and the formation of a hydrated alumina layer on the calcium aluminate. These chemical reactions lead to shorter binding times because less overall water was needed to keep the mixture deflocculated in solution. This also led to a more dense, stronger cement which exhibits less shrinkage. CaAl microspheres were mixed with NaSi microspheres at various ratios in deionized water at 37° C. and measured the set time using the Gillmore Needle test. A set time of <30 min was achieved with a mixture of 40 mass % NaSi, compared to 1.5 hrs for 100 mass % CaAl. No setting was ever observed with the extremely water soluble NaSi, as the sodium would leach from the material, leaving a silica gel.

Figures 3D, 3E:
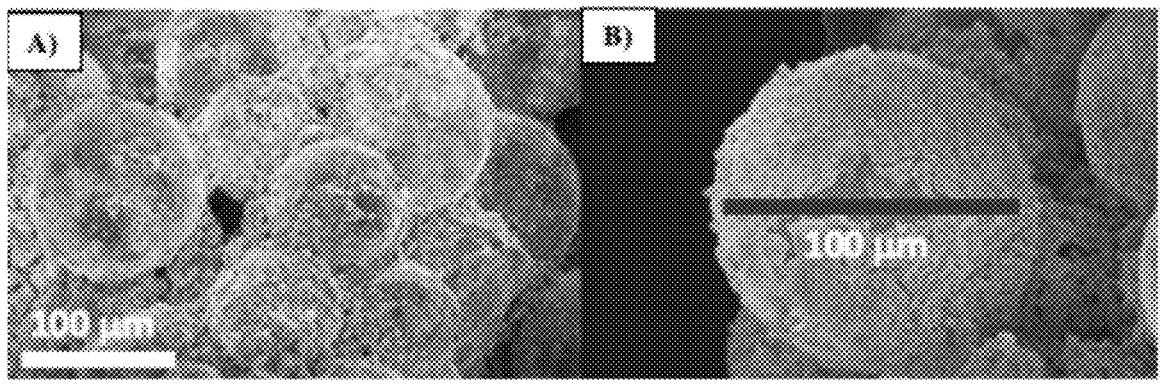
FIG. 3D is a micrograph of CaAl—NaSi microspheres after setting.
FIG. 3E is a micrograph of a microsphere after setting showing a crusted surface layer having a composition shown in FIG. 3F showing a hydrated metal oxide containing Na, Si, and Al. This layer and underlying microspheres will eventually convert into a biocompatible CBC.
Figure 3F:
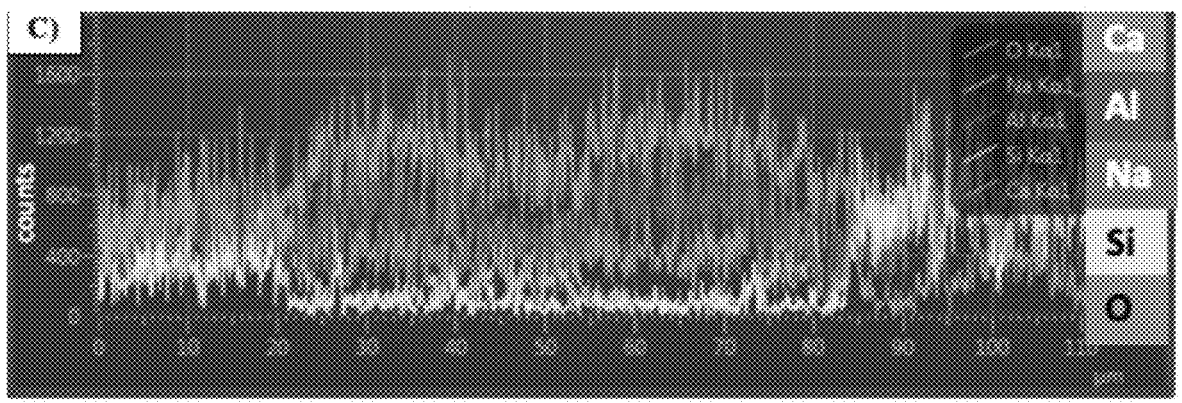
FIG. 3G is an SEM of a set composition of Example 1.
FIG. 3H is an SEM of a fully mature composition where the base material has fully decomposed into hydroxyapatite.

FIG. 3D shows a scanning electron microscope (SEM) image of microspheres after the initial set period. Energy dispersive spectroscopy (EDS) was performed on the microsphere shown in FIG. 3E across the break in the crust layer covering the sphere. The EDS spectra shown in FIG. 3F shows that a CaAl microsphere has been coated with a layer of a hydrated metal oxide containing Na, Si, and Al, which acts to initially set the material to a solid state that can withstand an appreciable load without deformation.

These microsphere-based CBCs can mature into a calcium deficient hydroxyapatite similar to MTA. Separation of the biocompatible elements into two main components can enable both quick setting and eventual hardening into a strong, chemically durable material. If left for longer time periods in water (e.g. 2-4 weeks), the microspheres shown in FIG. 3D will convert into chemically stable mature phases. However, in phosphate containing solutions, the material may mature into a calcium deficient hydroxyapatite. Such a final product would be similar to that observed with MTA but with a faster set time and much less complexity in the starting materials.

These biocompatible materials form into glasses to enhance swelling upon contact with water and reduce the set time. Using glasses instead of crystalline materials of the same chemistry can allow compositional flexibly and improvements in corrosion behaviors. The fit from the melt-derived materials can be sieved to 150 μm±10 μm. The fit and microspheres can be analyzed using optical microscopy and SEM to determine size and appearance, inductively coupled plasma mass spectrometry (ICPMS) to quantify (and confirm) the chemical composition, x-ray diffraction (XRD) to see if any crystallinity is present, fourier transform infrared spectroscopy (FTIR) and Raman to examine the chemical structure, Brunauer-Emmett-Teller (BET) analysis to determine surface area. An electrokinetic analyzer (EKA) can be used to determine the surface charge of the materials at physiological pH values. Since 50$Na_2O$ 50$SiO_2$ mol % is readily soluble in water, only the 33$Na_2O$ 64$SiO_2$ mol % glass will be used for this example because it will also exhibit a negative surface charge at physiological pH. Time-resolved recording of zeta potential changes and the analysis of the electrolyte solution after testing can provide information about the corrosion of the microspheres. Testing can be conducted in electrolyte solutions of 10 mM potassium chloride because it is the standard non-biological electrolyte solution and phosphate buffered saline because it is compatible with the pro-regenerative growth factors.

Growth factors BMP-2, VEGF, and G-CSF are mixed with the microspheres during setting and hardening. These growth factors were chosen based on their ability to promote dentinogenesis, revascularization and recruitment of progenitor cells respectively. Additionally, these factors have either a positive (BMP-2, VEGF) or negative (G-CSF) surface charge at physiological pHs, which affects how they load onto or release from the CaAl or 33$Na_2O$ 64$SiO_2$ mol % microspheres. First, the EKA is used to obtain an adsorption isotherm of the different growth factors onto the microspheres, at loading concentrations ranging from 10-500 μg/mL, as the zeta potential is measured with increasing progenitor concentration. This provides information about the density of the surface functional groups and what concentration of proregenerative can be adsorbed, and allows the optimization of initial loading concentrations for each growth factor based on the electrostatic interactions with the microsphere surfaces. Second, the adsorption kinetics are examined by taking a time-resolved recording of the changes in the zeta potential upon the addition of a chosen level of progenitor to the electrolyte solution. Because growth factor elution and corrosion will be occurring simultaneously, release kinetics are not examined using the EKA, but using ELISA. Growth factor loaded CBCs are placed in tissue culture media, incubated 5% $CO_2$ at 37° C., and their release of bound protein into this supernatant are quantified using commercially available ELISA kits for BMP-2, VEGF, and G-CSF.

Figures 3G, 3H:
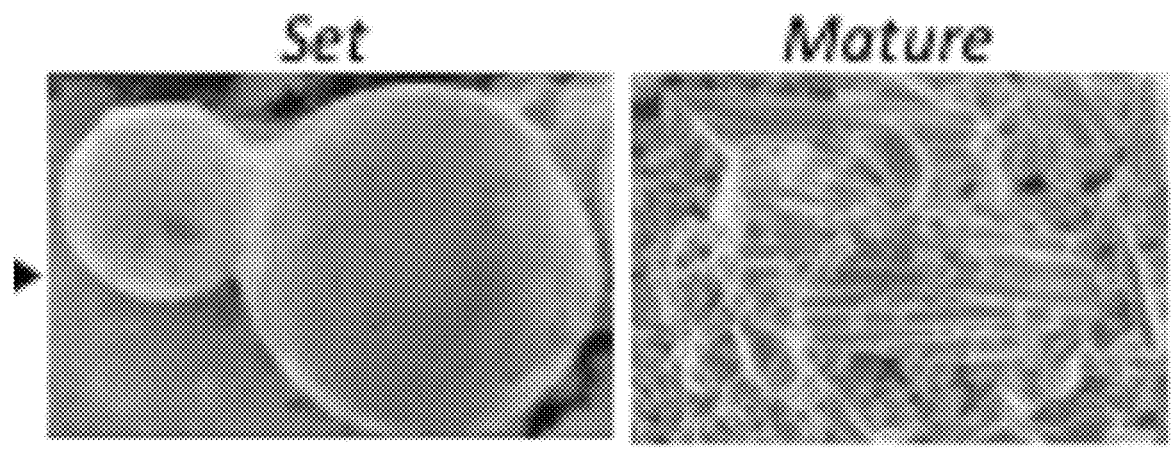

Whole supernatants are exchanged at 1, 12, 24 hours and 2, 5 and 7, 10 and 14 days and assayed, with the amount of released growth factor being expressed as a proportion of total growth factor loaded. The set and hardening times are quantified using the Gillmore needle test, and the hardened strength are examined using compression and flexure strength testing. FIG. 3G is an SEM of a set composition, while FIG. 3H is an SEM of a fully mature composition where the base material has partially decomposed into hydroxyapatite.

To fully characterize these materials, a full factorial study can be implemented using the following experimental conditions: 1) the material chemistry with levels between 50-50 CaAl—NaSi and 100-0 CaAl—NaSi, and 2) with mechanical testing after 2 hours, 1 week, 2 weeks. The material chemistry and material morphology are treated as discrete (i.e., category) variables and size distribution and incubation period as continuous variables. To prepare samples, microsphere-based CBCs are cast into rectangular beams (26×2×2 mm) and cylinders (6 mm dia.×12 mm height). The results of these experiments are analyzed with a one-way analysis of variance (ANOVA) and post-hoc Tukey's HSD statistical tests. In all cases, a value of $p<0.05$ are considered statistically significant. Statistical analysis of the results of each study can allow determination of both the individual effects of each variable and their relative contributions to the change in mechanical properties. This enables discernment of a generalized knowledge base for the mechanical properties of these CBC materials when compared to the current gold-standards of DYCAL and MTA.

In vitro efficacy and biocompatibility testing are conducted using cultures of characterized primary dental pulp progenitor cells (DPPCs) extracted from human third molars and GFP rats. To examine the biological efficacy of CBC bound growth factors, DPPCs are seeded in 12 well culture plates and placed in a modified Boyden chamber setup. Singly loaded CBCs containing either BMP-2, VEGF, or G-CSF and combined load CBCs containing all three, with loading concentrations optimized as described above are formed into 12 well inserts with 0.4 micron filter bases are placed on top of the cell containing wells. Unloaded CBCs serve as controls. Tissue culture medium are added and changed on a daily basis for the duration of the designated test period. The sample and cells are incubated for designated incubation periods up to 14 days in humidified air with 5% $CO_2$ at 37° C. mRNA are extracted from DPPCs at (1, 3, 7, and 14 days) and the expression of pro-regeneration related marker of dentin-pulp complex matrices such as DSPP, OC, ON, Col type I and III, CD31, CD34 and PCNA are quantified by quantitative PCR. Actual protein expression of these markers is also confirmed by direct immunocytochemistry on seeded cells, and cell viability are examined by TUNEL assays and immunocytochemistry for cleaved Caspase-3. To assess the biocompatibility of CBCs in direct contact with DPPCs, both singly loaded and combined load CBCs are formed into set discs and placed in the bottom of 12 well plates and DPPCs are seeded directly on top of CBC discs, with unloaded discs serving as controls. Cell morphology/spreading on CBCs are visualized by SEM/AFM and assays for expression of pulp related markers and viability are performed as described above.

Biologically effective levels of growth factors can be delivered in an ex vivo model via these dental pulp compositions. Singly loaded CBCs with electrostatically bound BMP-2, VEGF and G-CSF and combined loaded CBCs containing all three growth factors in an ex vivo model of intact pulp tissue can better assess the delivery of these factors by CBCs in the context of complex pulpal tissue. This ex-vivo model has been extensively characterized and is known to maintain tissue viability and architecture, an intact odontoblast layer, continued collagen synthesis by odontoblasts for up to 21 days in culture. The release of the surface charge bound growth factors bound to microspheres applied to the core of dental pulp can lead to activation of repair pathways. This can also lead to an increase in the expression of dentin proteins by odontoblasts as well as pro-repair signals in the cells of the pulp core.

Figure 4A:
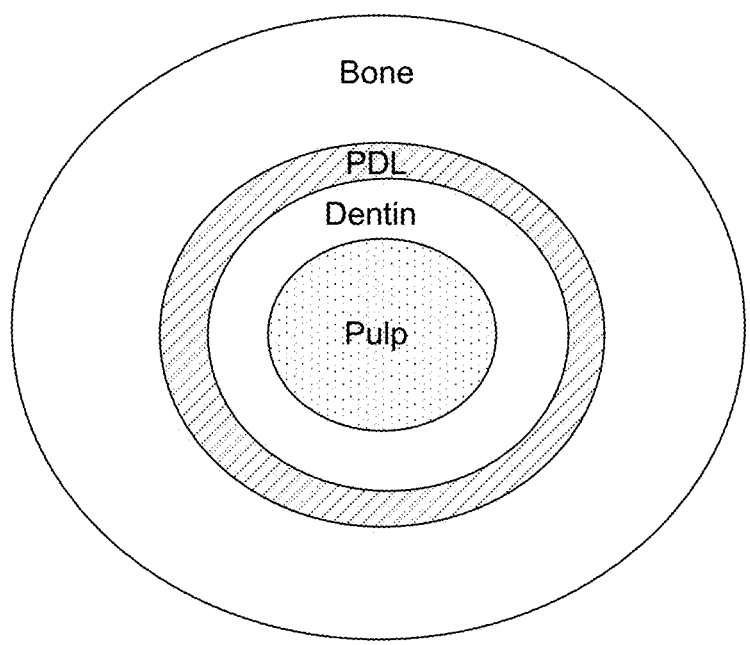
FIG. 4A is a schematic showing slices of a tooth segment, including the PDL surrounded by mandibular bone.
Figure 4B:
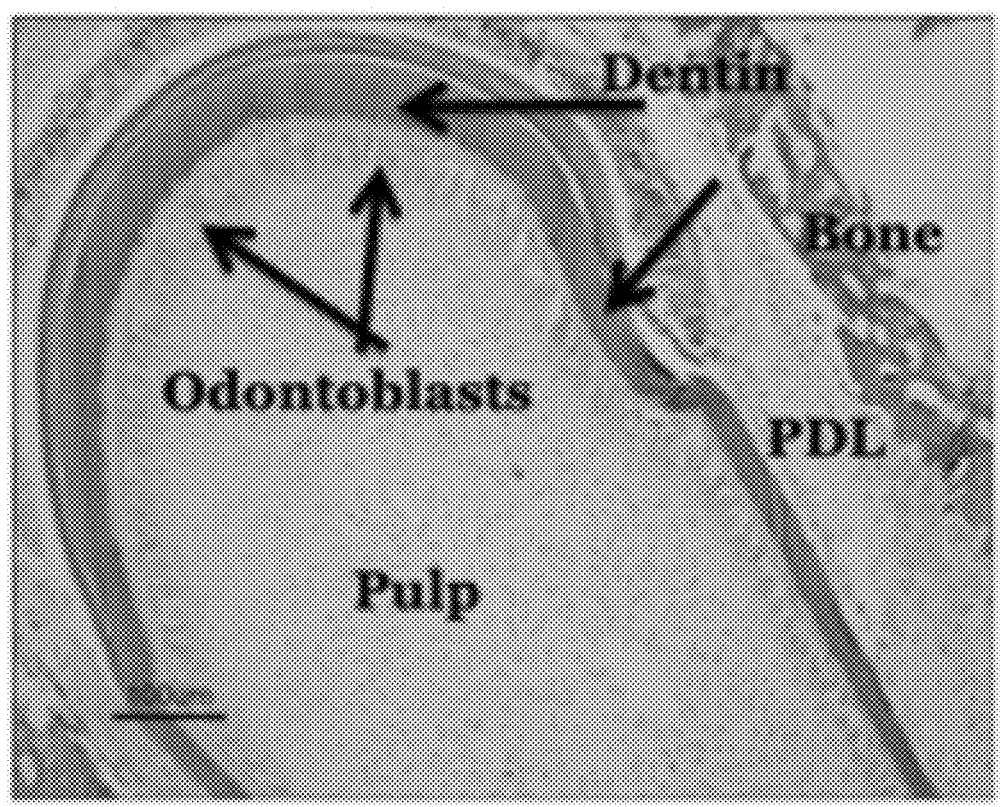
FIG. 4B is an H&E section of a rat mandible slice after 7 days in culture. Tissue architecture is maintained, as evidenced by an intact odontoblast cell layer and histologically normal pulp.
Figure 4C:
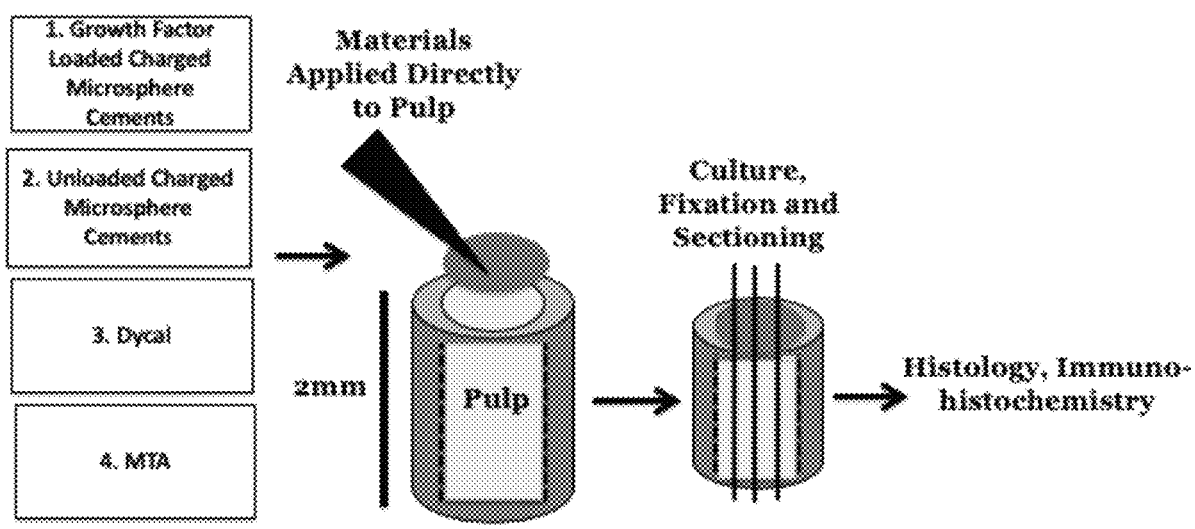
FIG. 4C is a schematic showing application of the various materials to the ex vivo organ culture model mandible. Mandible slices are capable of surviving up to 21 days in culture with minimal losses in viability and the continued preservation of tissue architecture.
Figure 5:
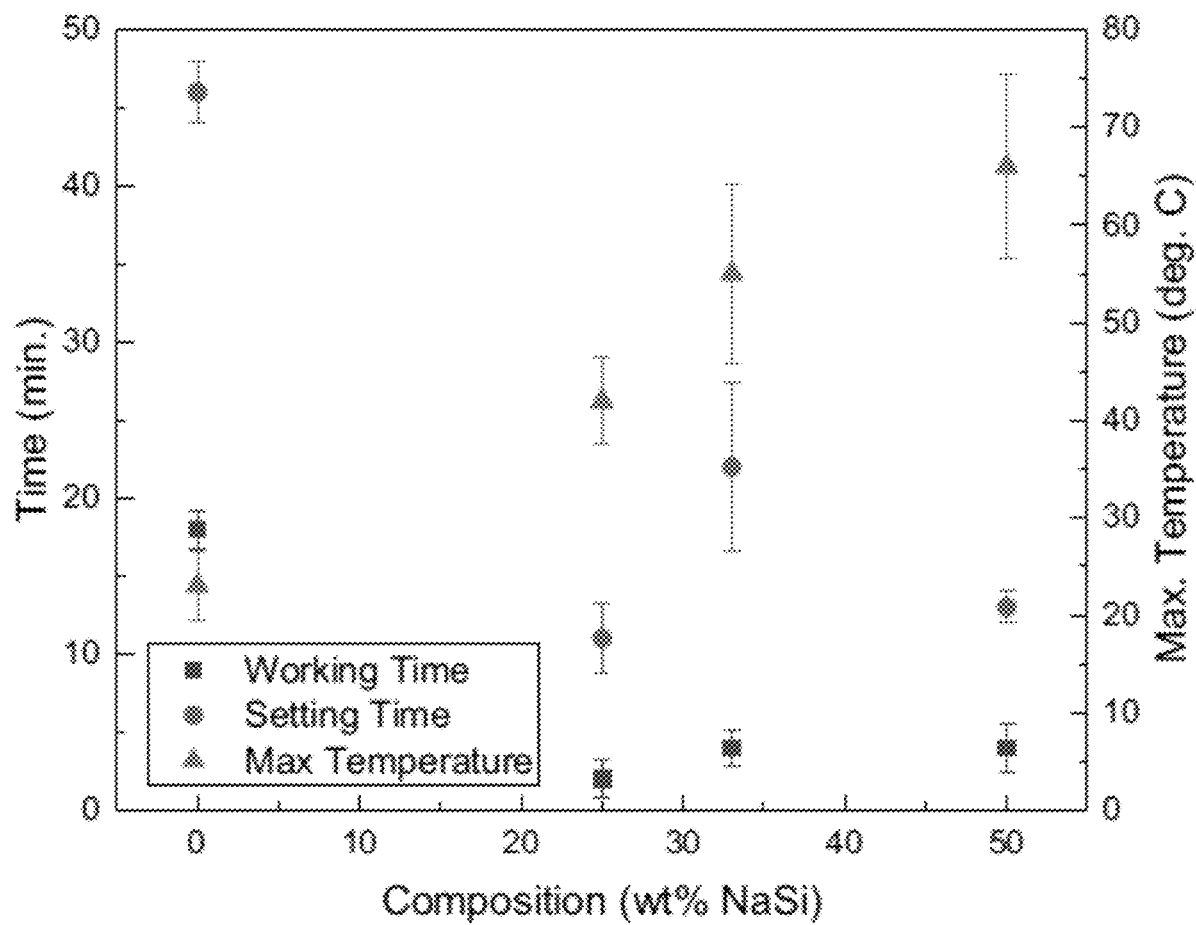
FIG. 5 is a graph of working and setting times for multiple NaSi—CaP cements, and average maximum temperature reached during setting.
Figure 6A:
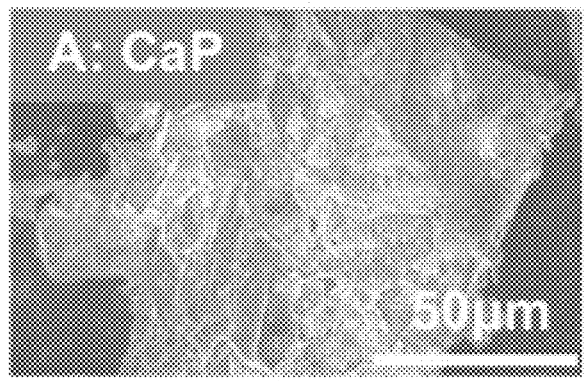
FIG. 6A-6E are SEM of NaSi—CaP cement compositions 24 h after setting where CaP (a), 25NaSi (b), 33NaSi (c), 50NaSi (d), and NaSi (e).
Figure 6B:
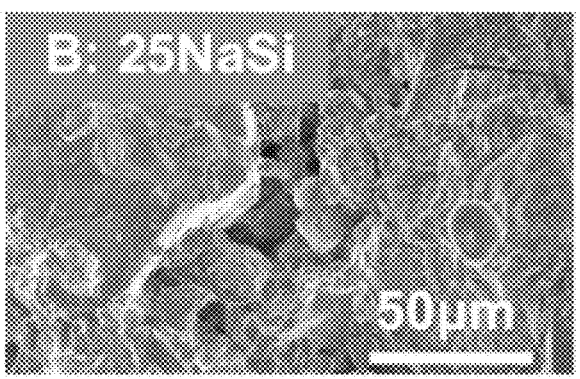
Figure 6C:
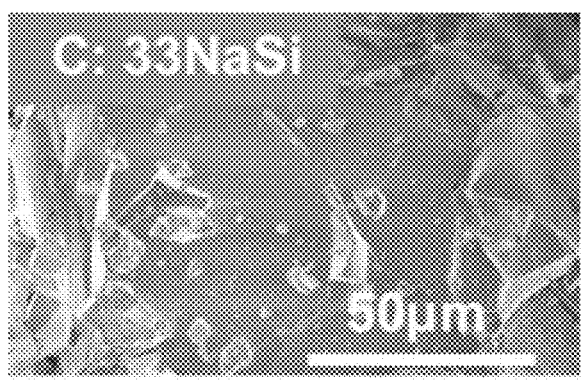
Figure 6D:
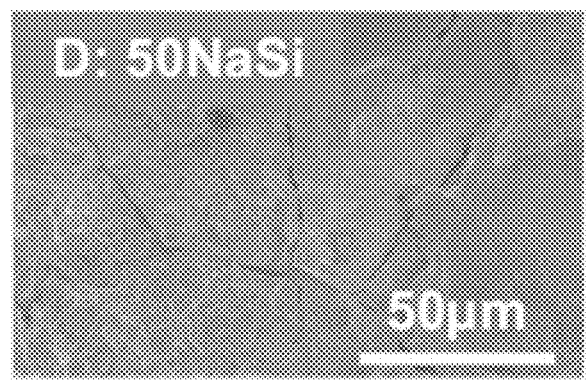
Figure 6E:

Rat mandibles are dissected from 28 day old male Wistar rats and sliced into 2 mm sections on a rotary bone saw, which allows direct access to the dental pulp. FIG. 4A is a schematic showing sections of a tooth segment including PDL surrounded by mandibular bone. Growth factor loaded (single and combined) CBCs are applied as caps directly to the exposed dental pulp of each mandible section. DYCAL, MTA and unloaded charged microsphere-based CBCs are applied as controls. After 1, 5, 7 and 14 days of culture, mandible slices are fixed, demineralized and paraffin embedded for sectioning. Lengthwise sections are taken in order to maximize visualization of the pulp area in contact with the applied material as illustrated in FIG. 4C.

Sections are examined using scanning electron microscopy in order to observe microstructural changes in the pulp and dentinal tissues in apposition to the applied materials. Histological examination of mandible slice sections after H&E staining allow the tissue structure in apposition to the applied materials to be observed, and the level of tissue repair or damage assessed as the result of their application as shown in FIG. 4B. Additionally, immunolocalization of key markers of tissue repair allows the efficacy of the both loaded and unloaded microsphere-based CBCs and conventional pulp capping materials to be compared. A significant increase in the expression of key indicators of tissue repair would be expected such as DSPP, OC, OP, and Collagen types I and III, as well as histological evidence of cell migration/differentiation in response to growth factor loaded microsphere-based CBCs compared to unloaded microsphere-based CBCs, MTA or DYCAL.

Cytotoxicity to the pulp from any of the applied materials is assessed by immunohistochemical staining for cleaved Caspase III and TUNEL assays. Positive expression of biomarkers are semi-quantified by image sampling and computerized image analysis.

Example 2

A blend of sodium metasilicate (NaSi) and calcium phosphate (CaP) glasses was prepared in several ratios. The sodium metasilicate (NaSi) glass was made by melting a sodium bicarbonate (Alfa-Aesar, Ward Hill, Mass., USA) with silica ($SiO_2$) powder (Alfa-Aesar, Ward Hill, Mass., USA) at 1100° C. for 1 h. A composition of 50 mol % $Na_2O$-50 mol % $SiO_2$ was selected for its proximity to the maximum solubility of sodium in the network. The calcium phosphate (CaP) glass was synthesized by melting monocalcium phosphate monohydrate [$Ca(H_2PO_4)_2 \cdot H_2O$] powder (Alfa-Aesar, Ward Hill, Mass., USA) at 1100° C. for 1 h. Melts were quenched on a stainless-steel plate and the resulting glass was ground into frit. Granules were sieved to a particle size distribution between 106 and 150 µm using 3" diameter test sieves. The results of this process were granules of NaSi and CaP glasses.

Cements were prepared for setting measurements by mechanically mixing different masses of NaSi and CaP powders (Table 1).

TABLE 1

| Sample | Composition |
| --- | --- |
| 25NaSi | 25 wt % NaSi |
|  | 75 wt % CaP |
| 33NaSi | 33 wt % NaSi |
|  | 67 wt % CaP |
| 50NaSi | 50 wt % NaSi |
|  | 50 wt % CaP |

NaSi glasses were prepared at 50 mol % $Na_2O$-50 mol % $SiO_2$, while CaP glasses were prepared at 33 mol % CaO-67 mol % $P_2O_5$.

Deionized (DI) water was then added to initiate the setting reaction. A powder-to-liquid (P/L) ratio of 2.5 g mL-1 was chosen for all testing as it produced pastes that were easily manipulated while holding their shape without slumping under their own weight.

A procedure for determining the working and setting time of the cements was adapted from ISO 9917-1:2017 for the testing of water-based dental cements. The working and setting times were recorded as the time elapsed between the end of mixing and the time when the needle failed to make a complete circular indentation in the cement. The experiments were carried out a total of three times.

Sealing ability was measured by placing a sample of pulp-capping cement in methylene blue dye for a predefined period and measuring the depth of dye penetration.

To examine in vitro phase maturation behavior, a sample of each NaSi—CaP cement composition was mixed and allowed to set for 24 h before being placed in 2 mL of a phosphate buffered saline (PBS) solution with a pH of 7.2. Cements were incubated for 7 days at 37° C. The samples were then removed, dried, and the microstructure was observed using SEM. Samples were then crushed into a fine powder and examined using XRD and ATR-FTIR.

The gradual appearance of characteristic peaks from one phase as the other decreases in ATR-FTIR spectra indicates that the glasses are only physically mixed and not chemically reacting in ambient conditions. Exothermic reactions occurred upon mixing the NaSi—CaP cements with water. NaSi concentrations in the range of 25-50 wt % provided cements with desirable consistencies: a smooth putty that could be formed into a shape and would not slump under its own weight. Note that preliminary testing demonstrated that compositions with greater than 50 wt % NaSi had the consistency of wet sand and would not hold their shape. The mean working time of the pure CaP was significantly higher than those of the glass mixtures. The CaP had a working time of 18±1.2 min. The addition of the NaSi drastically reduced the working time to between 2-5 min. No statistical difference was observed in the working time of the glass mixtures.

While no statistically significant variation was seen in working time, setting times differed with NaSi concentration. The setting time of the CaP was 46±2.0 min. 25NaSi had a setting time of 11±2.2 min, which lacks statistically significant differences when compared to the setting time of 50NaSi, which had a value of 13±1.0 min. The setting time of 33NaSi, which was statistically significantly higher than the other two glass mixtures, was 22±5.4 min. While the mean working times of 25NaSi, 33NaSi, and 50NaSi lack statistically significant differences, the mean setting time of 33NaSi is statistically significantly higher than the other two compositions. The results showed that working times remain constant in the range of 25 to 50 wt % NaSi, while setting time varies. Working time is longest for 0 wt % NaSi but decreases to under 5 min in samples with 25-50 wt % NaSi.

SEM examination of the glass mixtures after setting provided insight into the working and setting behavior (FIGS. 3A-3F). For pure CaP (FIG. 3A), individual granules are still visible that show slight degradation. This observation correlates well to the subjective properties of the bulk sample observed during handling in which the sample readily crumbles as particles appear to be only loosely held together. Pure NaSi has the exact opposite appearance (FIG. 3E) in that all the granules have completely degraded into a hydrated matrix with a relatively smooth, solid surface. This observation explains the behavior of the bulk sample, which never fully sets. These samples were observed to remain pliable even after 1 month in the incubation cabinet at 37° C.

The cements that were a mixture of CaP and NaSi had an appearance similar to the parent materials; the 25NaSi was largely granular while 50NaSi appears similar to the pure NaSi but with a slightly rougher surface. The 33NaSi had a blend of CaP granules suspended in hydrated matrix of NaSi. These images also correlate to the behavior of the bulk samples. Pure CaP has a chalky texture after setting and crumbles easily during handling. The addition of NaSi appears to make the set samples more physically robust, as particles are not shed from the surfaces of these samples during handling and they cannot be easily crushed in the hand. Set NaSi—CaP cements are white in color and visually homogeneous.

ATR-FTIR spectra taken after setting showed that chemical changes in the cements occurred during setting. These results show that cement samples set as Si—O—Si linkages are formed in the hydrated matrix and as CaP particles begin to corrode. X-ray diffraction of set samples did not show formation of crystalline phases during setting.

The sealing capabilities of the various cements varied with NaSi concentration. The results of this experiment show that the addition of NaSi within certain compositional ranges improves the sealing ability of CaP glass. Specifically, NaSi from about 25% to less than 50% performed well. It appears that less than about 25% had poor structural integrity (i.e. loosely bound particles), while about 50% and above exhibited undesirable absorption of water and swelling.

Upon one week of incubation in PBS, all compositions showed peaks indicative of crystallization, with amorphous regions still evident between 20-40° 2θ. Identified crystalline phases are presented in Table 3.

TABLE 3

| Sample name | Identified phases |
| --- | --- |
| CaP | $Ca(H_2PO_4)_2 \cdot H_2O$ |
|  | $Ca_3H_2(P_2O_7)_2 \cdot 4H2O$ |
| 25NaSi | Brushite, $CaHPO \cdot 2H_2O$ |
| 33NaSi | Canaphite, $CaNa_2P_2O_7 \cdot (H_2O)_4$ |
| 50NaSi | Canaphite, $CaNa_2P_2O_7 \cdot (H_2O)_4$ |
|  | $Na_4P_2O_7 \cdot (H_2O)_{10}$ |

The NaSi—CaP cements in this example had working times in the range of 2-5 min and setting times between 10-25 min. Notably, no organic resins or separate catalysts are needed to initiate setting.

In the NaSi glass, there is a 1:1 molar ratio between $Na_2O$ and $SiO_2$, causing the typically highly connected, covalently bonded Si—O network to form isolated $SiO_4$ tetrahedra. Bonding in these glasses occurs through Van der Waals forces between the sodium ions, which easily corrode upon exposure to water to form a hydrated matrix. CaP glasses are also susceptible to aqueous attack, although to a much lesser extent than the NaSi. In this case, the phosphate glasses are composed of a cross-linked network of tetrahedral with a non-bridging oxygen at one vertex of each $PO_4$ group. The introduction of calcium ions increases the quantity of non-bridging oxygens, depolymerizing the network into linear chain structures. These long chains shorten as modifier content increases, reducing the network's durability. The initial stages of aqueous reactions result in the leaching of calcium from the surface of the glass to create a $P_2O_5$-rich surface layer The working and setting times of the NaSi—CaP cements are dictated by the physical structure provided by the slow-corroding CaP particles and the hydrated matrix formed by the NaSi that binds them together. For CaP, no temperature change was observed upon mixing with DI water and the set samples easily crumbled during handling. Investigation of the set sample with SEM showed that the individual particles were still visible with minimal surface corrosion. Therefore, the change in physical properties of the cement is attributed to hydration, swelling, and subsequent physical interlocking of the particles. The addition of NaSi in the range of 25 to 50 wt % drastically decreased the working and setting time due to the formation of the hydrated silica matrix and the physical interlocking of CaP particles. However, when NaSi content is >75 wt % the cements were never observed to set because they do not have the structure provided by the slow-corroding particles of CaP.

The linear trend observed in setting time with varying amounts of NaSi was not followed by the 25NaSi cement composition. 25NaSi appears to deviate from the general trend with a much lower setting time than either the pure CaP or 33NaSi compositions. The low setting time of 25NaSi appears to be due to the interactions between two factors: temperature and hydrated matrix formation. Generally, decreases in setting time and increases in temperature during setting correlate well with one another in that the corrosion of CaP is expected to be faster at higher temperatures. Though higher temperatures were reached in the 33NaSi and 50NaSi samples, the hydrated matrix formed by the dissolved NaSi quickly coated the CaP particles and appears to have inhibited their corrosion. Conversely, the NaSi present in the 25NaSi sample caused a sufficient increase in temperature to begin the corrosion of the CaP particles but did not form enough of a hydrated matrix to interfere with the reaction.

Additionally, it was observed that vibrations indicative of Si—O—Si linkages were more intense in the 25NaSi composition. This shows that in the 25NaSi samples, the lower number of sodium ions interact preferentially with the CaP before the SiO₄ tetrahedra. Unimpeded by the sodium, more of the SiO4 tetrahedra can interact to form Si—O—Si bonds, leading to a quicker setting time.

The chemical reaction responsible for setting continues to occur as mature phases are formed during the incubation of these cements. It is proposed that this process may be expressed by the following reaction:

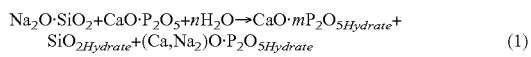  (1)

where m and n are constant moduli based on the relative amounts of CaO to $P_2O_5$ and $H_2O$ respectively. The products of this reaction are hydrated $SiO_2$, hydrated calcium phosphates, and hydrated calcium phosphates with a portion of the calcium ions substituted for pairs of sodium ions. In addition to the breakdown and release of sodium ions from the NaSi structure, the formation of products in the above reaction also produces heat.

Example 3

Figure 7:
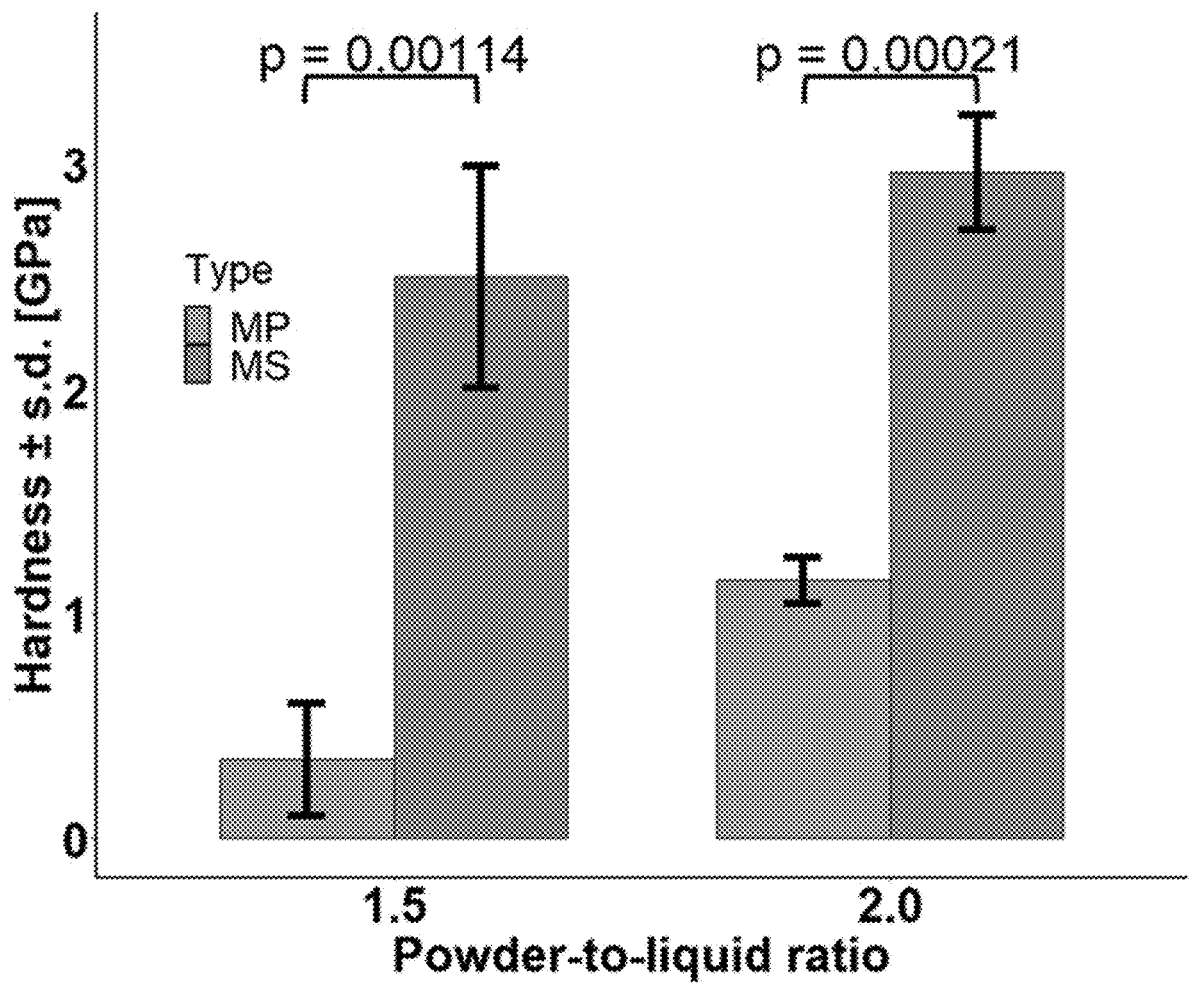
FIG. 7 is a graph of hardness for spheroidized microspheres and microparticles (frit).

Flame-spheroidized microspheres (MS) and microparticles (MP) of the same diameter (~100 um) were mixed in two different ratios of 1.5:1 and 2:1 (mixture of particles to DI water) and allowed to set for 24 hours. These cements included a mixture of pure CaP microspheres with sodium metasilicate ($Na_2SiO_3$) at a 3:1 ratio. After setting, the samples were nanoindented and results showed a statistically significant increase in the hardness in both cases as illustrated in FIG. 7. This increase in hardness is indicative of residual stresses created on the surface of the microspheres by the flame-spheroidization process. This shows that there is an increase in mechanical strength and hardness of the cement when using microspheres. Thus, control of surface morphology and mechanical hardness of the surface can be achieved. Mechanical properties of surfaces impact the viability of cells that attach and survive on a substrate. As a result, by controlling the mechanical properties of the surface the biological response of the surface can also be tuned.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

What is claimed is:

1. A dry powder dental pulp capping composition, comprising:
   a dry particulate base material which is non-toxic, and capable of forming a structural capping matrix, wherein at least 50% of the particulate base material is in the form of microspheres; and
   a dry particulate inorganic setting material which is non-toxic, water-soluble, biocompatible, and capable of setting the composition and initiable by adding water to the composition, wherein the dry particulate inorganic setting material is selected from the group consisting of metasilicate glass, bioactive borate glass, sodium silicate blend, potassium silicate, calcium silicate, borate glasses, $Na_2O$—$SiO_2$, $Na_2O$—CaO—$SiO_2$—$P_2O_5$, $Na_2O$—CaO—$B_2O_5$, $K_2O$—CaO—$B_2O_3$, NaSi glass, and combinations thereof.

2. The composition of claim 1, wherein at least 50% of the dry particulate inorganic setting material is in the form of microspheres.

3. The composition of claim 1, wherein one or both of the particulate base material and the dry particulate inorganic setting material comprise frit.

4. The composition of claim 1, wherein one or both of the particulate base material and the dry particulate inorganic setting material comprise microspheres having an average maximum particle dimension of 40 μm to 150 μm.

5. The composition of claim 1, wherein the particulate base material is selected from the group consisting of ceramics, glasses, crystalline materials, and combinations thereof.

6. The composition of claim 5, wherein the particulate base material is at least one of aluminate glass, silicate glass, phosphate glass, and composites thereof.

7. The composition of claim 5, wherein the particulate base material is at least one of calcium aluminate glass, mineral trioxide aggregate, $SiO_2$—CaO—$Na_2O$—$P_2O_5$ silica glass, $SiO_2$—CaO—$P_2O_5$ silica glass, calcium silicate glass, calcium phosphate silica glass, hydroxyapatite, calcium phosphate glass, and composites thereof.

8. The composition of claim 1, wherein the particulate base material comprises titanium which optionally further comprises a coating of hydroxyapatite or hydroxyapatite precursor on the titanium.

9. The composition of claim 1, wherein the particulate base material comprises 50% to 80% by weight of the composition.

10. The composition of claim 1, wherein the dry particulate inorganic setting material comprises 20% to 50% by weight of the composition.

11. The composition of claim 1, wherein the composition has a working time of at least one minute, and a setting time of less than 30 minutes.

12. The composition of claim 1, further comprising an additive selected from the group consisting of inert filler, pH control agent, setting time adjustment agent, colorant, antimicrobial, radiopacity agent, and combinations thereof.

13. The composition of claim 1, further comprising a growth factor.

14. The composition of claim 13, wherein the growth factor is selected from the group consisting of BMP-2, VEGF, G-CSF, TGFβ1, FGF-2, PDGF, and combinations thereof.

15. The composition of claim 13, wherein the growth factor is distributed within the composition and associated with at least one of the particulate base material and the dry particulate inorganic setting material via electrostatic attraction or functionalization.

16. A method of restoring damaged tooth features, comprising:
   removing diseased and/or damaged portions of the tooth to expose a prepared tooth region;
   adding water to the composition of claim 1 to form a workable coherent paste;
   introducing the workable coherent paste into the prepared tooth region;
   shaping the workable coherent paste within the prepared tooth region; and
   setting the workable coherent paste to form a rigid biomimetic structure within the prepared tooth region.

17. The method of claim 16, wherein the water is deionized and sterile water comprising from 10% to 40% by weight of the workable coherent paste.

18. The method of claim 16, wherein the prepared tooth region includes a dental pulp and adjacent dentin such that the method is capping a dental pulp.

19. The method of claim 16, wherein the method is sealing a tooth root canal during an apicoectomy.

20. The method of claim 16, wherein the method is sealing a root perforation.

21. A dental pulp capping kit, comprising:
    the composition of claim 1; and
    instructions to add water to the dry composition to form a workable coherent paste.

22. A paste consisting of the composition of claim 1 and water.

23. The composition of claim 1, wherein the dry particulate inorganic setting material is $Na_2O$—$SiO_2$.

24. The composition of claim 23, wherein the $Na_2O$—$SiO_2$ comprises $Na_2O$ at a mole fraction from 25 mol % to 50 mol % and $SiO_2$ at a mole fraction from 50 mol % to 75 mol %.

25. The composition of claim 1, wherein the particulate base material is CaP.

26. The composition of claim 1, wherein the composition does not include an organic resin.

* * * * *